US00PP14676P29

(12) United States Plant Patent
Bergman

(10) Patent No.: US PP14,676 P2
(45) Date of Patent: Apr. 6, 2004

(54) CHRYSANTHEMUM PLANT NAMED 'YOFABIENNE'

(50) Latin Name: *Chrysanthemum×morifolium*
Varietal Denomination: Yofabienne

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,681

(22) Filed: Mar. 25, 2003

(51) Int. Cl.[7] ..... A01H 5/00

(52) U.S. Cl. ..... Plt./286

(58) Field of Search ..... Plt./286

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Chrysanthemum plant named 'Yofabienne', characterized by its compact, uniform, upright and outwardly spreading plant habit; strong and freely branching growth habit; small dark green-colored foliage; uniform flowering habit; early flowering habit; numerous small daisy-type inflorescences; red purple and white bi-colored ray florets; and excellent postproduction longevity with plants maintaining good substance and color for about three to four weeks in an interior environment.

1 Drawing Sheet

Botanical classification/cultivar designation: *Chrysanthemum×morifolium* cultivar Yofabienne.

BACKGROUND OF THE INVENTION

The present Invention relates to a new and distinct cultivar of Chrysanthemum plant, botanically known as *Chrysanthemum×morifolium* and hereinafter referred to by the name 'Yofabienne'.

The new Chrysanthemum is a product of a planned breeding program conducted by the Inventor in Salinas, Calif. and Fort Myers, Fla. The objective of the breeding program is to create new compact potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in May, 1997, in Salinas, Calif., of a proprietary Chrysanthemum seedling selection identified as code number YB-6500, not patented, as the female, or seed, parent with the Chrysanthemum cultivar Chantal, disclosed in U.S. Plant Pat. No. 7,516, as the male, or pollen, parent. The new Chrysanthemum was discovered and selected by the Inventor as a single flowering plant within the progeny of the stated cross grown in a controlled environment in Fort Myers, Fla. in March, 1998. The selection of this plant was based on its uniform plant growth habit, desirable inflorescence form and ray floret colors, fast response time, and excellent postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yofabienne has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yofabienne'. These characteristics in combination distinguish 'Yofabienne' as a new and distinct Chrysanthemum:

1. Compact, uniform, upright and outwardly spreading plant habit.
2. Strong and freely branching growth habit.
3. Small dark green-colored foliage.
4. Uniform flowering habit.
5. Early flowering, 6.5-week response time.
6. Numerous small daisy-type inflorescences.
7. Red purple and white bi-colored ray florets.
8. Excellent postproduction longevity with plants maintaining good substance and color for about three to four weeks in an interior environment.

Plants of the new Chrysanthemum differ primarily from plants of the female parent selection in ray floret coloration as plants of the new Chrysanthemum have red purple and white bi-colored ray florets whereas plants of the female parent selection have pink-colored ray florets. In addition, plants of the new Chrysanthemum flower about three to four days later than plants of the female parent selection.

Plants of the new Chrysanthemum differ primarily from plants of the male parent, the cultivar Chantal, in ray floret coloration as plants of the new Chrysanthemum have red purple and white bi-colored ray florets whereas plants of the cultivar Chantal have white-colored ray florets. In addition, plants of the new Chrysanthemum flower about three or four days earlier than plants of the cultivar Chantal, and inflorescences of plants of the new Chrysanthemum do not produce pollen whereas inflorescences of plants of the cultivar Chantal produce pollen.

Plants of the new Chrysanthemum can be compared to plants of the cultivar Dark Cherie, disclosed in U.S. Plant Pat. No. 8,830. In side-by-side comparisons conducted in Salinas, Calif., plants of the new Chrysanthemum differed from plants of the cultivar Dark Cherie in the following characteristics:

1. Plants of the new Chrysanthemum flowered more uniformly than plants of the cultivar Dark Cherie.
2. Plants of the new Chrysanthemum flowered about 1.5 weeks earlier than plants of the cultivar Dark Cherie.
3. Plants of the new Chrysanthemum had smaller inflorescences than plants of the cultivar Dark Cherie.
4. Plants of the new Chrysanthemum had red purple and white bi-colored ray florets whereas plants of the cultivar Dark Cherie had pink-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of typical flowering plants of 'Yofabienne' grown as spray-types.

The photograph at the bottom of the sheet comprises a close-up view of typical inflorescences of 'Yofabienne' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the fall in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 21 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Yofabienne.

Commercial classification: Daisy-type potted Chrysanthemum.

Parentage:

*Female, or seed, parent.*—*Chrysanthemum×morifolium* seedling selection identified as code number YB-6500, not patented.

*Male, or pollen, parent.*—*Chrysanthemum×morifolium* cultivar Chantal, disclosed in U.S. Plant Pat. No. 7,516.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous daisy-type potted Chrysanthemum that is typically grown as a spray-type. Compact, uniform with lateral branches upright and outwardly spreading; uniformly mounded crown. Strong and freely branching growth habit; about six lateral branches develop after removal of terminal apex (pinching); dense and full plants.

*Plant height.*—About 20.5 cm.

*Plant width.*—About 31 cm.

*Lateral branches.*—Length: About 16 cm. Diameter: About 3 mm. Internode length: About 1.2 cm. Strength: Strong. Texture: Pubescent. Color: Close to 146A.

*Foliage description.*—Arrangement: Alternate; simple. Length: About 3.4 cm. Width: About 2.6 cm. Apex: Cuspidate. Base: Truncate. Margin: Palmately lobed, sinuses between lateral lobes parallel to overlapping. Texture, upper surface: Sparsely pubescent. Texture, lower surface: Pubescent; veins prominent. Color: Developing and fully expanded foliage, upper surface: 147A. Developing and fully expanded foliage, lower surface: 147B. Venation, upper surface: 147B. Venation, lower surface: 147C. Petiole length: About 1.2 cm. Petiole diameter: About 2 mm. Petiole color, upper and lower surfaces: 147B to 147C.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences not fragrant. Plants are typically grown as spray-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about 6.5 weeks later.

*Postproduction longevity.*—Inflorescences maintain good color and substance for about three to four weeks in an interior environment.

*Quantity of inflorescences.*—Very freely flowering, about 20 inflorescences develop per lateral branch.

*Inflorescence bud.*—Height: About 3 mm. Diameter: About 4 mm. Shape: Oblate. Color: Between 146A and 147A.

*Inflorescence diameter.*—About 2.7 cm.

*Inflorescence depth (height).*—About 9 mm.

*Diameter of disc.*—About 1.2 cm.

*Receptacle diameter.*—About 3.5 mm.

*Ray florets.*—Shape: Elongated oblong. Orientation: Initially upright, then perpendicular to the peduncle. Aspect: Mostly straight and flat. Length: About 1.3 cm. Corolla tube length: About 2.5 mm. Width: About 4 mm. Apex: Rounded to emarginate. Base: Fused into a corolla tube. Margin: Entire. Texture: Smooth, glabrous, velvety. Number of ray florets per inflorescence: About 22 arranged in a single whorl.

Color: When opening and fully opened, upper surface: Towards margins, close to 155D; center, 155D overlain with darker than 71A; towards base, close to 155D. When opening and fully opened, lower surface: Close to 155D underlain with darker than 77A.

*Disc florets.*—Arrangement: Massed at center of receptacle. Shape: Tubular, elongated. Apex: Five-pointed. Length: About 4 mm. Diameter, apex: About 1 mm. Diameter, base: Less than 1 mm. Number of disc florets per inflorescence: About 85. Color: Immature: Close to 154A to 9A. Mature: Apex: 9A to 12A. Mid-section: Lighter than 144D. Base: Close to 155D.

*Peduncles.*—Length: First peduncle: About 3.3 cm. Fourth peduncle: About 4.4 cm. Seventh peduncle: About 5.7 cm. Diameter: About 1.5 mm. Angle to vertical: About 45° from vertical. Strength: Strong, flexible. Texture: Pubescent. Color: 146A.

*Phyllaries.*—Quantity per inflorescence: About 24. Length: About 3.5 mm. Width: About 1.5 mm. Shape: Deltoid. Apex: Acute. Base: Truncate. Margin: Entire. Texture, upper surface: Waxy, smooth. Texture, lower surface: Pubescent. Color, upper surface: Between 146A and 147A. Color, lower surface: 147A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Yofabienne', as illustrated and described.

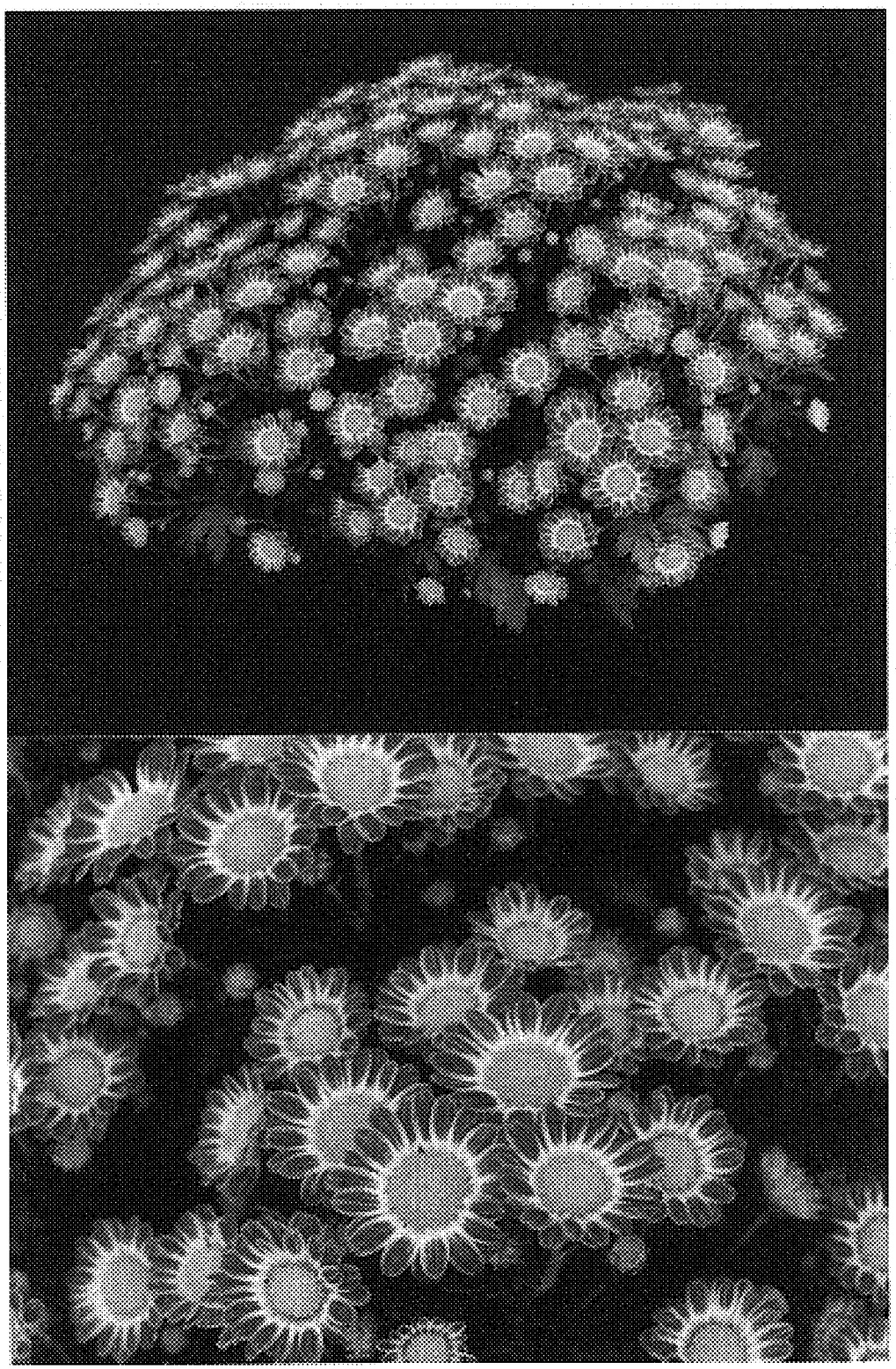

* * * * *